US005971969A

United States Patent [19]

Cashel

[11] Patent Number: 5,971,969

[45] Date of Patent: *Oct. 26, 1999

[54] PORTABLE RECEPTACLE FOR RECEIVING AND CONTAINING EMESIS

[76] Inventor: Karen A. Cashel, 1611 Diamond Dr., Newtown, Pa. 18940

[ * ] Notice: This patent is subject to a terminal disclaimer.

[21] Appl. No.: 09/015,872

[22] Filed: Jan. 29, 1998

[51] Int. Cl.[6] .......... A61M 1/00

[52] U.S. Cl. .......... 604/323

[58] Field of Search .......... 604/317, 323, 604/326, 327, 355; 128/760, 766, 771; 383/28, 35–36; 4/144.2, 144.3

[56] References Cited

U.S. PATENT DOCUMENTS

| | | |
|---|---|---|
| Re. 29,321 | 7/1977 | Holbrook . |
| 618,624 | 1/1899 | Stanek et al. . |
| 3,646,935 | 3/1972 | Holbrook et al. . |
| 3,797,734 | 3/1974 | Fleury et al. . |
| 3,832,738 | 9/1974 | Kliemann . |
| 3,920,179 | 11/1975 | Hall . |
| 4,238,448 | 12/1980 | Salvadori et al. . |
| 4,394,928 | 7/1983 | Philip . |
| 4,930,997 | 6/1990 | Bennett . |
| 4,950,247 | 8/1990 | Rosenblatt . |
| 4,990,145 | 2/1991 | Fleury . |
| 4,995,386 | 2/1991 | Ng . |
| 5,045,076 | 9/1991 | Pierce . |
| 5,049,273 | 9/1991 | Knox . |
| 5,050,616 | 9/1991 | Wolff et al. . |
| 5,062,835 | 11/1991 | Maitz et al. . |
| 5,067,821 | 11/1991 | Young . |
| 5,098,418 | 3/1992 | Maitz et al. . |
| 5,112,322 | 5/1992 | Hathaway . |
| 5,171,224 | 12/1992 | Tucker . |
| 5,188,622 | 2/1993 | Müller et al. . |
| 5,331,689 | 7/1994 | Haq . |

OTHER PUBLICATIONS

Sporty's Pilot Shop, "Little John & Convenience Bag", p. 70, Nov. 1995–Feb. 1996.

*Primary Examiner*—Corrine McDermott
*Assistant Examiner*—David J. Cho
*Attorney, Agent, or Firm*—R. Neil Sudol; Henry D. Coleman

[57] ABSTRACT

A portable receptacle for receiving and containing emesis has a main body member defining an emesis containment chamber, a neck connected to the main body member, and a mouthpiece attached to the neck at an end thereof opposite the main body member. The neck defines a conduit communicating with the chamber. A baffle structure and/or one-way valve is positioned substantially within the conduit to allow emesis to move therethrough into the chamber and to minimize spillage and leakage outwardly through the conduit from the chamber.

19 Claims, 1 Drawing Sheet

PORTABLE RECEPTACLE FOR RECEIVING AND CONTAINING EMESIS

BACKGROUND OF THE INVENTION

The present invention deals with the field of devices utilized in the health care field generally for receiving bodily fluids. Devices for this purpose have been used primarily in hospitals but also in doctors' facilities and smaller clinics and the like. Currently, it is common to use basins, which are open, shallow, kidney-shaped, plastic pans for collection of bodily fluids, such as sputum and emesis. The present device is specifically usable for collecting of emesis. This is particularly important in view of disease control considerations, such as the likelihood that emesis might contain blood, which may present a risk of contamination by HIV, Hepatitis B, and/or pathogens not carried in the blood. As such, the present invention provides a unique configuration solely utilized for the purposes of safe and efficient gathering and containment of potentially dangerous spewed emesis.

OBJECT OF THE PRESENT INVENTION

An object of the present invention is to provide a container for receiving and retaining emesis.

Another object of the present invention is to provide such a container wherein the chance of emesis escape or spillage is minimized if not eliminated.

A further object of the present invention is to provide such a container which is easy to use.

Yet another object of the present invention is to provide such a container which is easily emptied.

It is an additional object of the present invention to provide such a container which is easily secured, for example, to hospital beds.

These and other objects of the present invention will be apparent from the drawings and descriptions herein.

SUMMARY OF THE INVENTION

A portable receptacle for receiving and containing emesis comprises, in accordance with one embodiment of the present invention, a main body member defining an emesis containment chamber, a neck connected to the main body member, and a mouthpiece attached to the neck at an end thereof opposite the main body member. The neck defines a conduit communicating with the chamber. A baffle structure is positioned substantially within the conduit to allow emesis to move therethrough into the chamber and to minimize spillage and leakage outwardly through the conduit from the chamber.

In accordance with a specific feature of the present invention, the baffle structure includes a plurality of baffle plates positioned in the conduit. The baffle plates may be angularly oriented with respect to the conduit such as to extend downstream therealong. The baffle plates are preferably fixed to the neck.

A portable receptacle for receiving and containing emesis comprises, in accordance with another embodiment of the present invention, a main body member defining an emesis containment chamber, a neck connected to the main body member, and a mouthpiece attached to the neck at an end thereof opposite the main body member. The neck defines a conduit communicating with the chamber. A one-way valve is positioned substantially within the conduit to allow emesis to move therethrough into the chamber and to minimize spillage and leakage outwardly through the conduit from the chamber.

In accordance with another feature of the present invention, applicable in either embodiment, the mouthpiece has a form substantially conforming to a face of a user about the user's mouth, thereby facilitating a substantial seal or closure between the user's face and the neck. The mouthpiece may be rotatably movably mounted with respect to the neck to facilitate engagement thereof with respect to the mouth of a patient.

Pursuant to another feature of the present invention, the neck and the conduit are oriented obliquely with respect to the main body member to facilitate flow of emesis through the conduit into the chamber.

A handle is advantageously secured to the main body member to facilitate holding and stabilizing of the main body member during usage of the portable emesis receptacle. The handle may cooperate with the main body member to define a least one vertically extending slot to facilitate a mounting of the portable receptacle.

According to furthers feature of the present invention, measurement indicia markings are provided on the main body member to facilitate measurement of the amount of material within the chamber, the main body member defines an exit opening therein in fluid flow communication with the chamber to facilitate removal of material therefrom, and a mouthpiece cap is detachably positionable selectively in engagement with the mouthpiece and extending thereover for closing thereof to facilitate retaining of emesis within the chamber of the main body member. The mouthpiece cap is adapted to extend over the mouthpiece for selectively closing the mouthpiece to prevent emesis passing outwardly through the mouthpiece. Also a mouthpiece cap attachment line may be secured to the mouth piece cap and attached to the neck in order to facilitate retainment of the mouthpiece cap with respect to the portable receptacle and minimize the chance of loss thereof during any extended time of non use.

The main body member of a portable receptacle in accordance with the present invention is mostly opaque but includes a translucent section which includes a plurality of measurement indicia markings to facilitate the measurement of the amount of total fluid volume within the emesis containment chamber at a given time.

DETAILED DESCRIPTION OF THE PREFERRED EMBODIMENT

Figure 1:
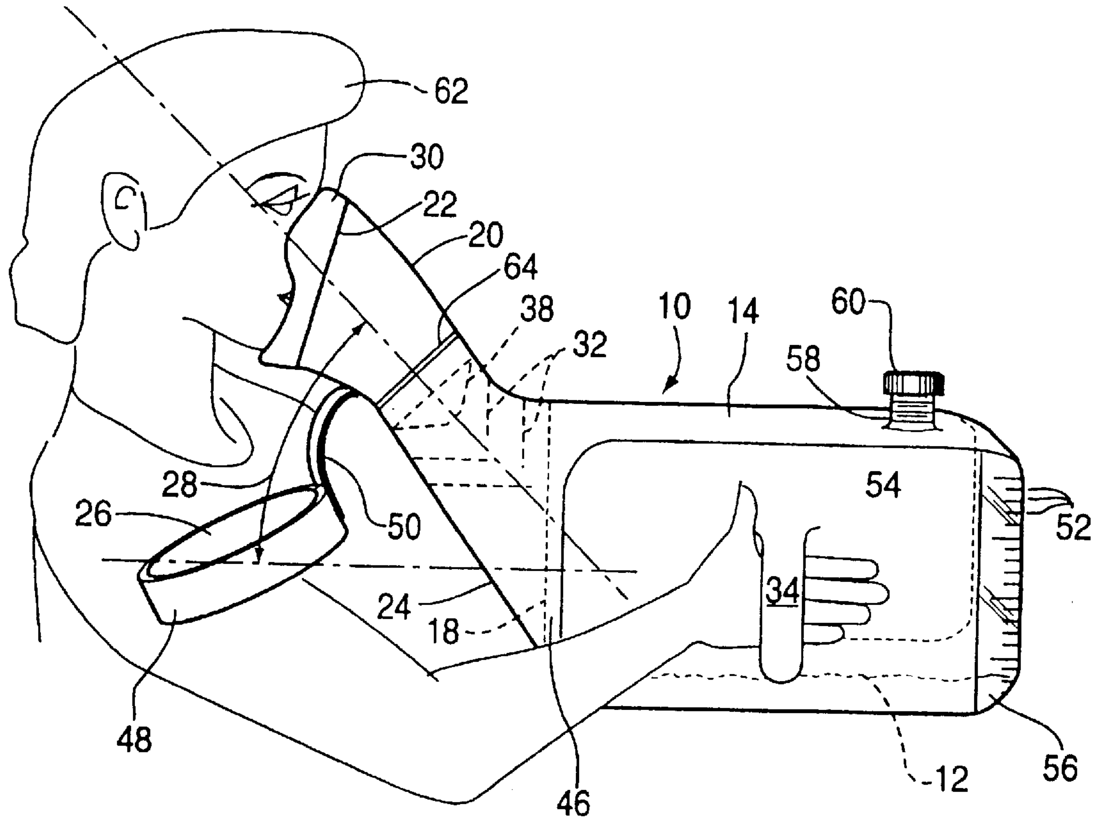
FIG. 1 is a front perspective illustration of an embodiment of the portable receptacle for receiving and containing emesis made in accordance with the present invention shown in usage by a patient or user.
Figure 2:
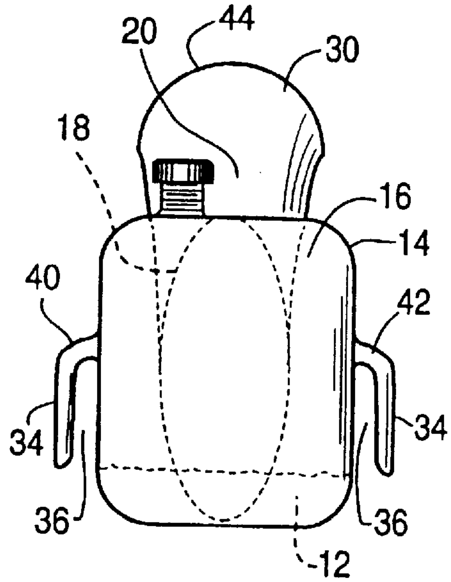
FIG. 2 is a side view of embodiment shown in FIG. 1 taken from the right.
Figure 3:
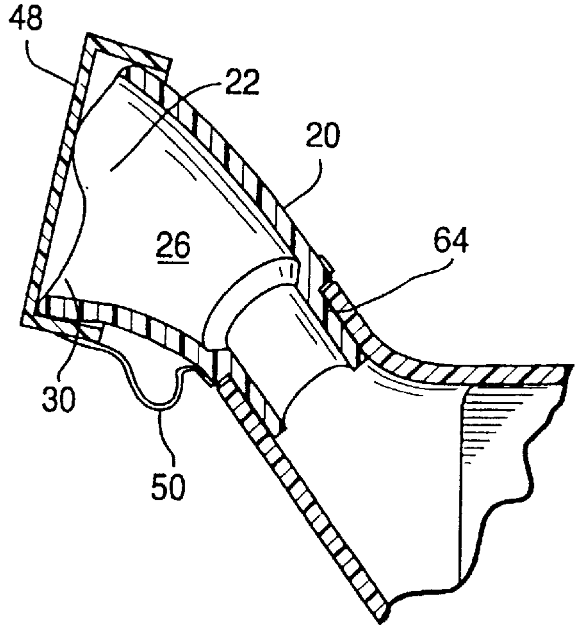
FIG. 3 is a side plan view of the neck piece and the mouth area of an embodiment of the present invention showing the mouthpiece cap in position extending over the mouthpiece area.

The present invention provides a new and useful improvement in gathering and disposing of emesis for use in hospitals, doctors' offices, clinics or even home environments. Numerous precautions are being published especially for use by health care workers as dictated by the Center for Disease Control to aid in the collection of various body fluids including emesis. Current disease control requirements, including preventative measures, have been significantly made more important by the significant presence of highly communicable diseases in society, such as HIV and Hepatitis B.

The present invention provides a portable receptacle 10 designed to accumulate emesis 12. Receptacle 10 includes a main body member 14 which defines an emesis containment chamber 16 therein. This emesis containment chamber 16 is designed to receive and contain emesis 12 and facilitate disposal thereof.

Main body member 14 defines a channel opening 18 preferably defined in a sidewall 46 thereof. This chamber opening 18 is in fluid flow communication with the emesis containment chamber 16 to facilitate the flow of emesis therein. A neck member 20 which preferably includes a neck conduit 26 extending therethrough from a neck inlet 22 to a neck outlet 24 is included in the apparatus of the receptacle 10. Neck member 20 is preferably at an angular orientation 28 of, preferably 30 to 60 degrees with respect to the main body member 14 and in particular with respect to the sidewall 46 thereof.

A mouthpiece 30 may be positioned over the neck inlet 22 to facilitate engagement thereof with respect to the mouth of a patient or user 62. Furthermore the mouthpiece 30 will preferably include an arcuate mouth engaging edge 44 adapted to contact the mouth area of the patient or user 62 in surrounding relationship to the user's mouth in order to facilitate receiving and containing of emesis 12 spewed therefrom.

The neck conduit 22 will preferably include therein a rigid differential flow control structure in the form of baffle plates 32 which are angularly oriented with respect to the neck conduit 26 such as to extend downstream therealong. The baffle plates 32 are designed preferably to allow emesis to be spewed from the neck inlet 22 through the neck conduit 26 to the neck outlet 24 and on into the emesis containment chamber 16 but to prevent similar reverse flow and thereby minimize spillage as well as minimizing any possibility of splashing. To further facilitate containment and prevent spillage and splashing a one-way valve 38 can optionally be included in the apparatus of the present invention. The one-way valve 38 is designed to allow emesis spewed through the neck conduit 26 at high speed to pass therethrough but to prevent reverse flow or reverse spillage outwardly through the neck conduit 26 from the outlet 24 to the inlet 22.

As an additional element of protection, a mouthpiece cap 48 may be positionable in engagement with the mouthpiece 30 to extend over the neck inlet 22 for closing thereof to prevent spillage of emesis 12 after usage of the portable receptacle 10. In order to prevent loss of the mouthpiece cap 48, a mouthpiece cap attachment line 50 may optionally be included which is attached with respect to the receptacle 10 and also with respect to the mouthpiece cap 48.

To facilitate holding of the receptacle 10 during usage, a handle means 34 may be included which may take the form of a first handle member 40 positioned on one side of the main body member 14 and a second handle member 42 positioned on the other opposite side of the main body member 14. In this manner a user can put his hands on both handles and rest the main body member 14 on his lap or abdomen for fixed holding thereof during the spewing of emesis 12.

Preferably the main body member 14 is generally opaque throughout in order to prevent direct viewing of the emesis 12 contained therein to make usage of the device more aesthetically pleasing. However, it is important under many circumstances that a doctor have an accurate measurement of the fluid volume of spewed emesis 12. For this reason the opaque areas 54 of the main body member 14 will preferably not include a section thereof positioned along the measurement indicia markings 52. This marking section 56 of the main body member 14 will preferably be defined as a translucent marking section to facilitate the viewing of the level of liquid within the emesis containment chamber 16 immediately adjacent the measurement indicia marking 52 to thereby determine the total fluid volume of spewed emesis 12.

The emptying of the emesis from the emesis containment chamber 16 can be achieved through the neck conduit 26 if desired. However, to further facilitate emptying of the containment chamber 16 an additional exit opening 58 may be optionally included with an exit cap member 60 engageable therewith for closing of the exit during usage and opening of the exit 58 whenever it is desired to empty the emesis containment chamber.

One of the unique aspects of the present invention is the orientation of the neck 20 and particularly the neck conduit 26 at an angle of 30 to 60 degrees with respect to the main body 14 and particularly with respect to the sidewall 46 thereof. This angular orientation when used in combination with the universal mouthpiece 30 allows usage by virtually any patient. Also, the downwardly extending baffle plates 32 allow movement of fluid into the emesis containment chamber 16 and prevent movement outwardly therefrom during the spewing of emesis 12 and thereafter during movement of the portable receptacle 10 to a disposal location. The transport of any filled container other than the receptacle 10 of the present invention to a location where it can be emptied is often difficult and risks contaminating because of the numerous types of body fluids which are often contained with emesis 12 and therefore contained within the containment device. The apparatus of the present invention is small enough to be used in households as well as in ambulances and clinics and is certainly capable of being used in hospital and other similar environments.

What is claimed is:

1. A portable receptacle for receiving and containing emesis comprising:

a main body member defining an emesis containment chamber;

a neck connected to said main body member, said neck defining a conduit communicating with said chamber;

a mouthpiece attached to said neck at an end thereof opposite said main body member; and a baffle structure positioned substantially within said conduit to allow emesis to move therethrough into said chamber and to minimize spillage and leakage outwardly through said conduit from said chamber, said baffle structure including at least one baffle plate positioned in said conduit with an angular orientation with respect to said conduit such as to extend downstream therealong.

2. The portable receptacle for receiving and containing emesis as defined in claim 1, further comprising a one-way valve disposed in said conduit.

3. The portable receptacle for receiving and containing emesis as defined in claim 1 wherein said mouthpiece has a form substantially conforming to a face of a user about the user's mouth, thereby facilitating a substantial seal or closure between the user's face and said neck.

4. The portable receptacle for receiving and containing emesis as defined in claim 3 wherein said mouthpiece is rotatably movably mounted with respect to said neck to facilitate engagement thereof with respect to the mouth of a patient.

5. The portable receptacle for receiving and containing emesis as defined in claim 1 wherein said baffle structure is fixed to said neck.

6. The portable receptacle for receiving and containing emesis as defined in claim 1 wherein said neck and said conduit are oriented obliquely with respect to said main body member to facilitate flow of emesis through said conduit into said chamber.

7. The portable receptacle for receiving and containing emesis as defined in claim 1, further comprising a handle secured to said main body member to facilitate holding and stabilizing of said main body member during usage of the portable emesis receptacle.

8. The portable receptacle for receiving and containing emesis as defined in claim 7 wherein said handle cooperates with said main body member to define a least one vertically extending slot to facilitate a mounting of the portable receptacle.

9. The portable receptacle for receiving and containing emesis as defined in claim 1 further comprising measurement indicia markings on said main body member to facilitate measurement of the amount of material within said chamber.

10. The portable receptacle for receiving and containing emesis as defined in claim 1 wherein said main body member defines an exit opening therein in fluid flow communication with said chamber to facilitate removal of material therefrom.

11. The portable receptacle for receiving and containing emesis as defined in claim 1 further comprising a mouthpiece cap detachably positionable selectively in engagement with said mouthpiece and extending thereover for closing thereof to facilitate retaining of emesis within said chamber of said main body member.

12. A portable receptacle for receiving and containing emesis comprising:

a main body member defining an emesis contnent chamber;

a neck connected to said main body member, said neck defining a conduit communicating with said chamber;

a mouthpiece attached to said neck at an end thereof opposite said main body member; and differential flow control means for permitting fluid flow in one direction through said conduit from said mouthpiece towards said chamber and for impeding fluid flow in an opposite direction through said conduit from said chamber towards said mouthpiece, said differential flow control means being disposed in said conduit to allow emesis to move therethrough into said chamber and to minimize spillage and leakage outwardly through said conduit from said chamber.

13. The portable receptacle for receiving and containing emesis as defined in claim 12 wherein said mouthpiece has a form substantially conforming to a face of a user about the user's mouth, thereby facilitating a substantial seal or closure between the user's face and said neck.

14. The portable receptacle for receiving and containing emesis as defined in claim 13 wherein said mouthpiece is rotatably movably mounted with respect to said neck to facilitate engagement thereof with respect to the mouth of a patient.

15. The portable receptacle for receiving and containing emesis as defined in claim 12 wherein said neck and said conduit are oriented obliquely with respect to said main body member to facilitate flow of emesis through said conduit into said chamber.

16. The portable receptacle for receiving and containing emesis as defined in claim 12 further comprising measurement indicia markings on said main body member to facilitate measurement of the amount of material within said chamber.

17. The portable receptacle for receiving and containing emesis as defined in claim 12, wherein said differential flow control means includes a one-way valve positioned substantially within said conduit.

18. The portable receptacle for receiving and containing emesis as defined in claim 12, wherein said differential flow control means includes at least one baffle plate positioned in said conduit with an angular orientation with respect to said conduit such as to extend downstream therealong.

19. A portable receptacle for receiving and containing emesis comprising:

a main body member defining an emesis containment chamber;

a neck connected to said main body member, said neck defining a conduit communicating with said chamber;

a mouthpiece attached to said neck at an end thereof opposite said main body member; and a substantially rigid structure positioned substantially within said conduit to allow emesis to move therethrough into said chamber and to minimize spillage and leakage outwardly through said conduit from said chamber, said structure being fixed relative to said neck and said container and asymmetrically disposed relative to a direction of fluid flow through said conduit from said mouthpiece toward said chamber so as to freely permit fluid flow through said conduit from said mouthpiece toward said chamber and to substantially prevent fluid flow through said conduit from said chamber toward said mouthpiece.

* * * * *